United States Patent [19]

Nakajima, deceased et al.

[11] Patent Number: 5,151,751
[45] Date of Patent: Sep. 29, 1992

[54] METHOD FOR EVALUATING COLOR TONE OF COATING FILM AND DEVICE FOR THIS EVALUATION

[75] Inventors: Takashi Nakajima, deceased, late of Ashiya, by Satoko Nakajima, legal representative; Misao Morita, Kobe, both of Japan

[73] Assignee: Nippon Paint Co., Ltd., Osaka, Japan

[21] Appl. No.: 553,823

[22] Filed: Jul. 18, 1990

[30] Foreign Application Priority Data

Jul. 19, 1989 [JP] Japan ................. 1-186699

[51] Int. Cl.⁵ .............. G01J 3/46; G01N 21/25; G01N 21/27
[52] U.S. Cl. .................. 356/402; 356/405; 356/446
[58] Field of Search ............ 356/402, 405, 446

[56] References Cited

U.S. PATENT DOCUMENTS 4,359,504 11/1982 Troy ...................... 428/403
4,479,718 10/1984 Alman .................... 356/405

FOREIGN PATENT DOCUMENTS 57-11014  3/1982  Japan .
59-180441 10/1984 Japan .
60-59866 12/1985 Japan .
62-160166 7/1987 Japan .
WO8100826 4/1981 PCT Int'l Appl. .

Primary Examiner—F. L. Evans
Assistant Examiner—K. P. Hantis
Attorney, Agent, or Firm—Armstrong, Nikaido, Marmelstein, Kubovcik & Murray

[57] ABSTRACT

A method giving a color tone-evaluating result which catches the deepness and transparency feelings of a coating film in an objective manner, and a device for use of this method. The evaluating results are obtained by projecting a luminous flux on a coating film, the high light saturation and/or high light excitation purity of the coating film are gotten on a basis of a high light part which is in an angle range of 5° to 15° against the regularly reflecting luminous flux in the reflecting light, and that, if necessary, the shade saturation and/or shade excitation purity are gotten on a basis of a shade part which is in an angle range exceeding 15°.

2 Claims, 7 Drawing Sheets

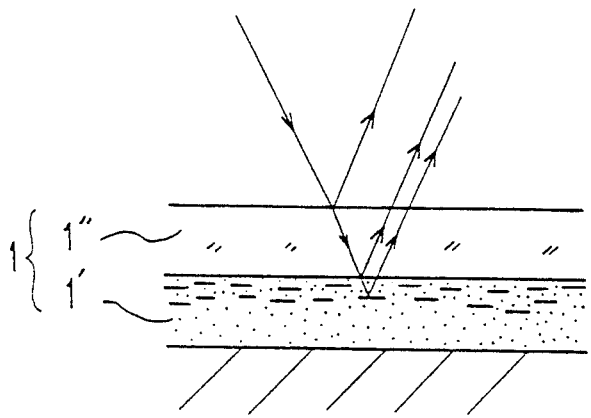 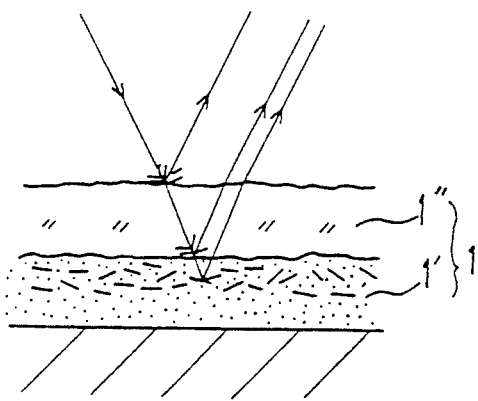
FIG.5(a)    FIG.5(b)
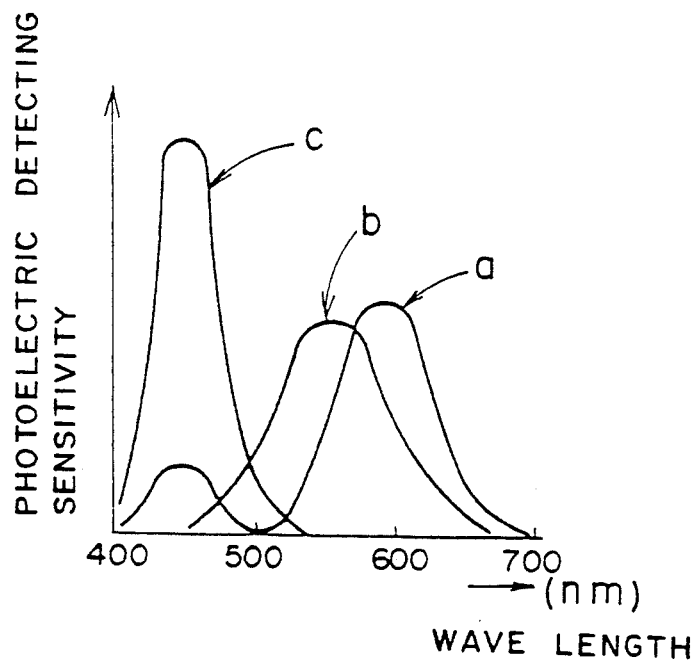
FIG.6

METHOD FOR EVALUATING COLOR TONE OF COATING FILM AND DEVICE FOR THIS EVALUATION

BACKGROUND OF THE INVENTION

The present invention relates to a method for evaluating a color tone of a coating film and a device for this evaluation.

As a coating film, there is a metallic film 1 made by that a paint containing a color pigment 11 and a gloss material 12 is applied as seen in FIG. 1, on which a clear paint is applied. Hereupon, the gloss material refers to a pigment in which alumina or a mica flake is a material and the surface emits gloss. A metallic film of this kind has practically been used, for example, as a coating film for an automobile body, so that it has a great effect on whether the outlook of an automobile is superior or inferior. Therefore, to make a reasonable relationship with this outlook, evaluation of a color tone of a coating film is very important.

Hitherto, the evaluation of a color tone of a coating film has been carried out according to the undermentioned methods.

That is, there are methods wherein, in a reflecting light upon projecting a luminous flux for a coating film, a high light part which is in an angle range adjacent to the regularly reflecting luminous flux, and a shade part which is in an angle range apart from said regularly reflecting luminous flux are separately and simply subjected to photoelectric detection, their luminous intensities are measured and the intensities obtained are treated with operation, and difference between the lightness of the coating film surface in a case of that the surface is seen from a direction adjacent to the regularly reflecting luminous flux and the lightness of the coating film surface in a case of that the surface is seen from a direction apart from the regularly reflecting luminous flux is investigated to evaluate the color tone of a coating film (Japanese Official Patent Provisional Publication, showa 59-180441; Japanese Official Patent Gazette, showa 57-11014; Japanese Official Patent Gazette, showa 60-59866; and Japanese Official Patent Provisional Publication, showa 62-160166).

In these previous methods, although an attempt to enhance accuracy for the evaluation is made by using a respectively proper equation in the operation treatment, all the methods are after all such that the color tone of a coating film is evaluated by simply looking at a difference between the luminous intensity at a high light part and the one at a shade part. The difference between the luminous intensity at a high light part and the one at a shade part appears as a contrast (flip-flop) feeling on a coating film surface. That is, the previous methods are that, if those are referred to a case of that an observer looks at an automobile body, a color tone is evaluated by that an extent of a contrast feeling on the body surface is expressed with an objective numeral value on a basis of the difference in the luminous intensities.

SUMMARY OF THE INVENTION

However, the results obtained from the evaluation in said previous methods can not be said to be in good agreement with evaluation results by an actual observer (a human's eye). That is, the human's eye takes a look at the contrast feeling which appears on a coating film surface as well as at a transparency (clarity) feeling and a deepness (depth-of-shade) feeling simultaneously, and thus the human carries out an evaluation for the appearance of the coating film, whereas the hitherto-known methods carry out the evaluation for the appearance on a basis of only the contrast feeling. Because of this, if a coating film which is ascertained as having a sufficient contrast feeling by the previous method is evaluated with a human's eye, a transparency feeling and a deepness feeling may be not enough and, as a result, the appearance may be judged as comprehensively insufficient.

According to a conclusion which the present inventors obtained, for the evaluation of the appearance of the coating film's surface it is important to objectively evaluate not only the contrast feeling but also the transparency and deepness feelings.

A coating film having a sufficient deepness feeling is strengthened with a feeling of that a light is coming from a deep place inside the coating film and, on the other hand, a coating film having a sufficient transparency feeling is strengthened with a feeling of that a transparent layer is piled on the coating film and, thus an observer looks at this coating film as having a rich color tone. Therefore, it is very important that an extent of the transparency feeling and the deepness feeling are expressed by objective numerals and that superiority or inferiority of of the appearance of the coating film is evaluated by these numerals.

According to said circumstances, the present invention has objects to provide a method giving a color tone-evaluating result which catches the deepness and transparency feelings of a coating film in an objective manner, and to provide a device for use of this method.

The present inventors made efforts to solve said subjects. As a result, it was discovered that the saturation and excitation purity obtainable with analysis of a reflecting light from a coating film surface is almost an index which indicates objectively the transparency and deepness feelings appearing on the coating film surface. The present invention was completed on a basis of the discovery.

To solve said objects, in the methods for evaluating a color tone of a coating film in the present invention, the color tone of a coating film is evaluated with the results obtained by that projecting luminous flux is applied for a coating film, the high light saturation and/or high light excitation purity of said coating film are gotten on a basis of a high light part which is in a range of 5° to 15° against the regularly reflecting luminous flux in the reflecting light, and that, if necessary, the shade saturation and/or shade excitation purity of said coating film are gotten on a basis of a shade part which is in a range exceeding 15° against said regularly reflecting luminous flux. In the method in the present invention, in addition to the above, at least one of color difference, lightness difference, and luminous intensity difference between a high light part and a shade part in a reflecting light may be derived and thus-derived result may be added to evaluation of the color tone of a coating film.

The device for evaluating a color tone of a coating film in the present invention is equipped with a light-projecting means with which a luminous flux for a coating film is projected, a spectral means with which a high light part and a shade part are spectroscopically separated, the former of which is in a range of 5° to 15° against a regularly reflecting luminous flux in a reflecting light of said luminous flux and the latter of which is in a range exceeding 15°, and also equipped with a photoelectric, detecting means with which these two lights separated with the spectral means are photoelectrically detected, an operation means with which both the detected signals being outputted from the photoelectric detecting means is inputted, the high light saturation and/or high light excitation purity of said coating film are derived with calculation from the photoelectrically detected signal in said high light part and the shade saturation and/or shade excitation purity of said coating film are derived with calculation from the photoelectrically detected signal in said shade part, and a presenting means with which the results derived from the operation means are presented.

In the device for evaluating a color tone of a coating film in the present invention, in addition to the above the operation means may be arranged so as to derive with calculation, on a basis of both the signals, at least one of color difference, lightness difference, and luminous intensity difference existing between a high light part and a shade part in a reflecting light. That is, because not only the luminous intensity difference, but also the color difference, light difference may be an index which represents the contrast feeling objectively, this contrast feeling may be added to the element necessary for evaluation of the color tone of a coating film.

A fundamental in the present invention is to carry out evaluation of the color tone of a coating film on a basis of the saturation and/or excitation purity which are obtained from a high light part and, if necessary, the saturation and/or excitation purity obtained from a shade part are referred as a supplement.

BRIEF DESCRIPTION OF THE DRAWINGS

FIGS. 5 (a) and (b) are crosssectional views which typically show a relation of a luminous flux projecting into a coating film with a reflecting light;

FIG. 6 is a graph which explains a spectral, photoelectric detection performance corresponding to a color matching function;

DESCRIPTION OF THE INVENTION

Figure 1:
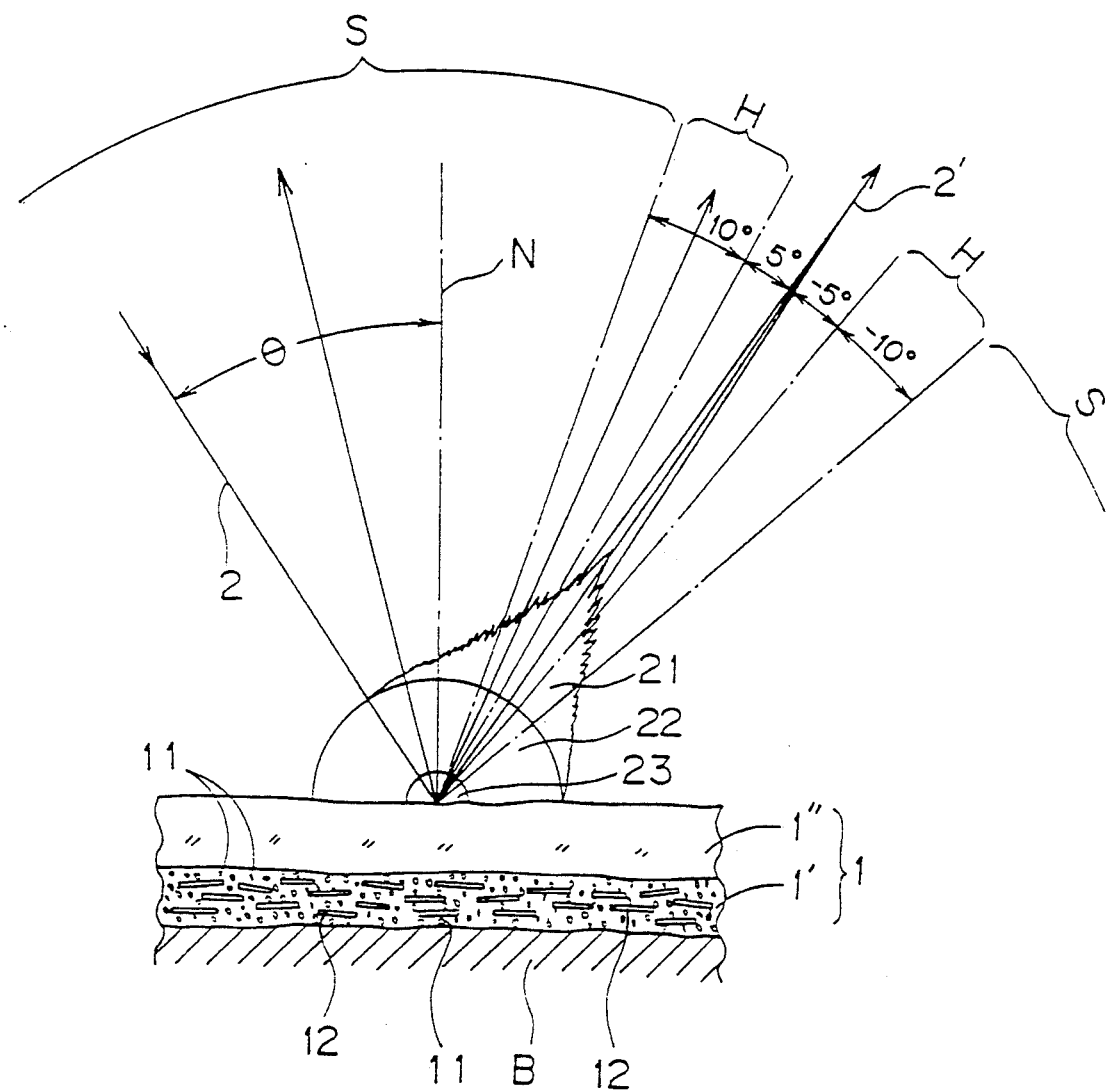
FIG. 1 is a diagram which typically explains a situation of a reflecting light being formed, when a luminous flux is projected to a coating film.

In the present invention, as seen in FIG. 1, the luminous flux 2 is projected for a coating film 1 set on a base material B. The coating film 1 consists of two layers which are a down layer 1' being formed by a paint containing a color pigment 11 and a gloss material 12 and an upper layer 1'' being formed by a transparent (clear) paint. As a reflecting light of the projecting luminous flux, in addition to a regularly reflecting luminous flux (specular reflection light) 2' there are a diffusing, reflecting light 21 arising from the gloss material 12, a diffusing reflecting light 22 arising from the colorant 11, and although it is in a small amount, a diffusing, reflecting light 23 on a surface of the upper layer 1'' as well. Besides, the projecting angle $\theta$ of a luminous flux being projected for the coating film 1 is in an angle range of 0° to 60°, usually taking as a standard a virtual vertical line N which stands on the coating film.

In these reflecting lights arising from said coating film, the high light saturation and/or high light excitation purity of the coating film 1 are derived as the data for evaluation from a high light part which is in an angle range H of 5° to 15° (+5° to +15°, −5° to −15°) against the regularly reflecting luminous flux 2' and also, the shade saturation and/or shade excitation purity of the coating film 1 are derived as the data for evaluation from a shade part which is in an angle range S exceeding 15° (over +15°, over −15°) against the regularly reflecting luminous flux 2' or, more preferably, from a shade part which is in an angle range of 45° to 135° (+45° to +135°, −45° to −135°) against the regularly reflecting luminous flux 2', although it depends upon the angle of incidence. If these data are available, evaluation which reflects the deepness and transparency feelings can be achieved.

Furthermore, at least one of the color difference, lightness difference, and luminous intensity difference existing between a high light part H and a shade part S in a reflecting light may be taken as data for evaluation. If the data are available, evaluation which reflects a contrast feeling can be made.

Figure 2:
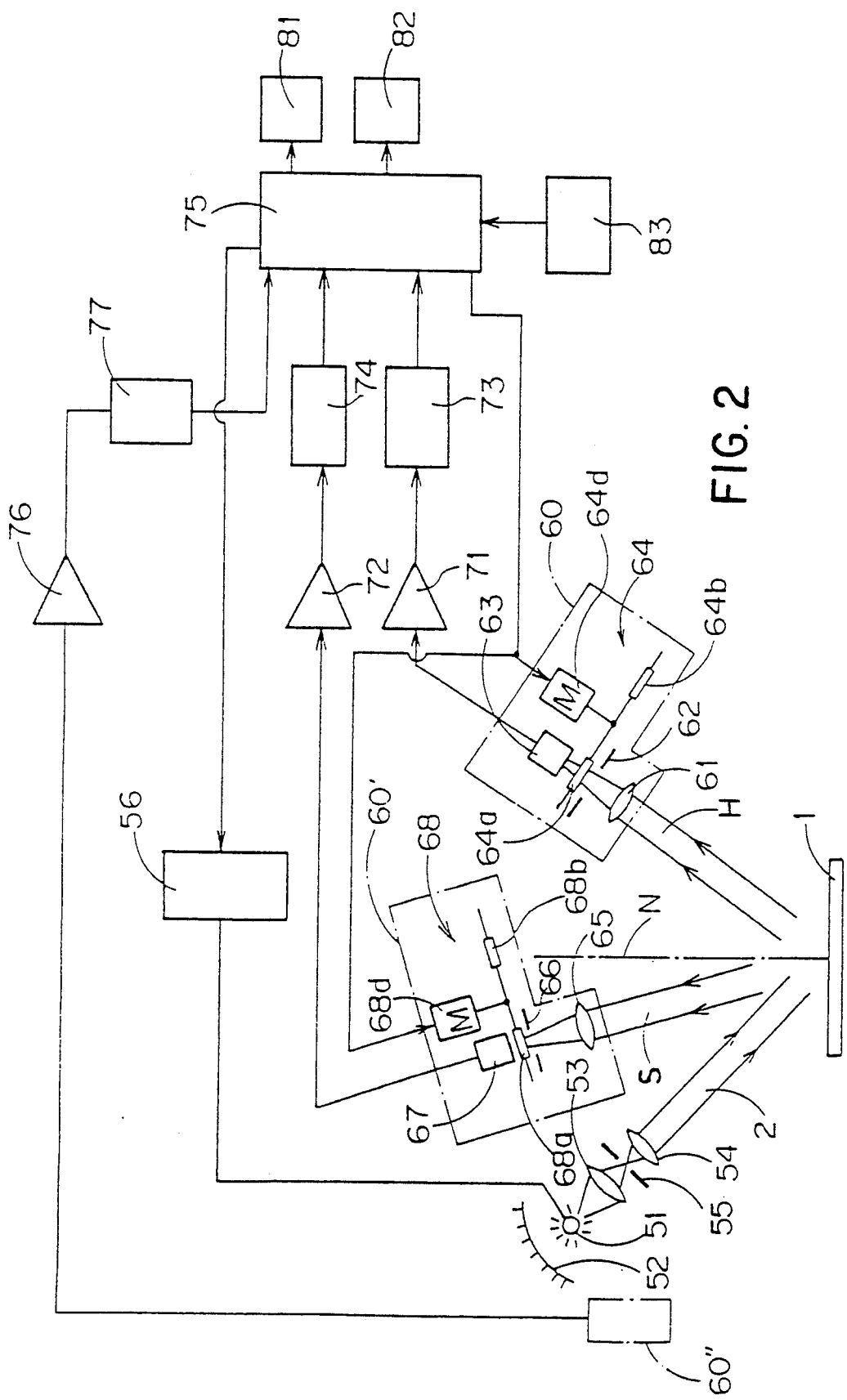
FIG. 2 is a block diagram showing a composition of one example of a device which is used in bringing a method for evaluating a color tone of a coating film in this invention into operation.

The data of saturation, excitation purity, color difference, lightness difference, luminous intensity difference and so on, as described above, can be obtained, for example, by using a device for evaluating a color tone of a coating film as shown in FIG. 2.

This device is equipped with a light-projecting means with which the projecting luminous flux 2 is projected for the coating film 1, a spectral means with which a high light part and a shade part in a reflecting light are respectively and spectroscopically separated, a photoelectrically detecting means with which the separated two lights are photoelectrically detected, a operation means with which the high light saturation and/or high light excitation purity of the coating film 1 are derive with calculation and the shade saturation and/or shade excitation purity of the coating film 1 are derived with calculation, and a presenting means with which the operation results are presented. Moreover, the operation means is able to derive with calculation at least one of the color difference, lightness difference, and luminous intensity difference existing between the high light part H and the shade part S in the reflecting light.

The light-projecting means is equipped with a light-projecting part consisting of a light source 51, a concave mirror 52, lens 53 and 54, and an iris 55. As the light source 51 are used a luminous source such as a tungsten halogen lamp, xenon lamp, pulse xenon arc lamp (a stroboscopic lamp).

The high light part (a high light reflecting light) passes through the lens 61 and iris 62, is separated with the spectral means 64, and then photoelectrically detected with a light detector element 63. The spectral means 64 is equipped with three filters 64a, 64b, and 64c (a diagram for 64c is omitted) and a switching motor 64d. Each filter differs in optical performance and, the photoelectric sensitivity performance including the filter and light source is made so as to get detecting signals which correspond to three stimulus values X, Y, and Z of the outputs coming from the light detector element 63. In other words, the whole spectral, detecting sensitivity performance consisting of combination of each filter, light source, and light detector element is conditioned so as to fit on the curves a, b, and c which are along the color matching function curve in FIG. 6. The curves a, b, and c correspond, respectively, to the stimulus values X, Y, and Z and, three detecting signals are outputted in series, simultaneously to switching of the filters with a motor M.

The shade part (a shade reflecting light) passes through the lens 65 and the iris 66, is separated with the spectral means 68, and then photoelectrically detected with the light detector element 67. The spectral means 68 is equipped with three filters 68a, 68b, and 68c (a diagram for 68c is omitted) and a switching motor 68d. The spectral means has a composition same to the spectral means 64 and, the phtoelectric detecting sensitivity including filters, similarly to the forementioned, is arranged so as to get detecting signals which correspond to three stimulus values X, Y, and Z of the outputs coming from the light detector element 67.

Needless to say, the light detector elements 63 and 67 need not to detect the whole light in the high light and shade parts and are enough with detecting only a part of the light. Besides, it are hoped that the spectroscopically detecting parts 60 and 60' circled with an one-point chain line in FIG. 2 is constructed so as to be able to move on a circle, of which center is the projecting point of the luminous flux 2 on the coating film 1, and that a range of the light detecting angle is adjustable.

The operation means consists of preamplifiers 71 and 72, A/D converters 73 and 74, and a microprocessor (CPU) 75.

The detecting signals from the light detector elements 63 and 67 are respectively amplified with the preamplifiers 71 and 72, converted into digits, and then inputted into the microprocessor 75. In the microprocessor 75, the undermentioned data are derived with calculation from three stimulus values of the high light part and those of the shade part inputted.

| Kinds of data derived with calculation |
| --- |
| High light saturation   $C^*ab$ (or $C^*uv$) |
| Shade saturation        $C^*ab$ (or $C^*uv$) |
| High light excitation purity   PH |
| Shade excitation purity        PS |
| Color difference        $\Delta E^*ab$ (or $\Delta E^*uv$) |
| Lightness difference    $\Delta L^*$ |
| However:   $C^*ab = (a^{*2} + b^{*2})^{\frac{1}{2}}$ |
| $C^*uv = (u^{*2} + v^{*2})^{\frac{1}{2}}$ |
| $L^*, a^*, b^*$; CIE 1967 $L^*a^*b^*$ color space |
| $L^*, u^*, v^*$; CIE 1967 $L^*u^*v^*$ color space |
| PH:   $(x - x_n)/(x_d - x_n) \times 100$, or |
| $(y - y_n)/(y_d - y_n) \times 100$ |
| PS:   $(x - x_n)/(x_d - x_n) \times 100$, or |
| $(y - y_n)/(y_d - y_n) \times 100$ |
| but,   $x = X/(X + Y + Z)$ |
| $y = Y/(X + Y + Z)$ |
| $x_n, y_n$ are chromaticity coordinates of a standard light used for measurements. |
| $x_d, y_d$ are chromaticity coordinates of an intersecting point of loci. |
| $\Delta E^*ab = [(\Delta L^*)^2 + (\Delta a^*)^2 + (\Delta b^*)^2]^{\frac{1}{2}}$ |
| $\Delta E^*uv = [(\Delta L^*)^2 + (\Delta u^*)^2 + (\Delta v^*)^2]^{\frac{1}{2}}$ |
| $L^* = 116 (Y/Y_0) - 16$ |

The data derived with calculation are presented on the presenting means such as a monitor 81 and a printer 82 in which a liquid crystal or a cathod-ray tube is used.

The operation means equipped with a key or a switch for operation is indicated with 83.

Besides, the spectrospically detecting part 60" has a composition similar to the spectrospically detecting parts 60 and 60', and its detecting signal is amplified by the preamplifier 76, converted into digits by the A/D converter, and then inputted into a microprocessor 75. In the microprocessor 75, it is judged whether or not the gloss of the light source 51 has a proper strength for photoelectric detecting in the spectrospically detecting parts 60 and 60'. This judgement undergoes a feedback to the light source gloss-controlling part 56 and, as a result, the light source is always maintained at a defined lightness.

Also, in said device the operation means may derive with calculation the difference in luminous intensities instead of the lightness and color differences.

The evaluation methods in the present invention need not to get data with said device. For example, the excitation purities may be derived in the undermentioned way.

Figure 7:
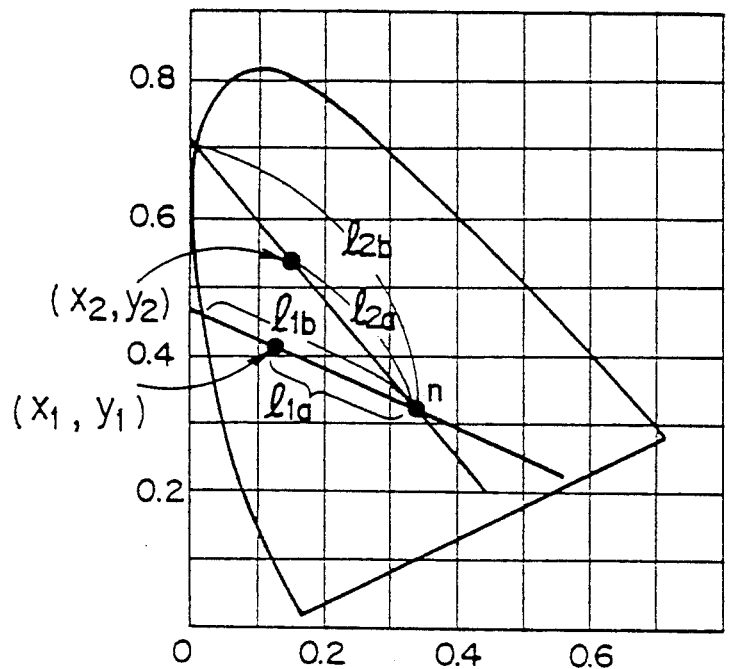
FIG. 7 is a graph which shows a chromaticity diagram which is used for measurement of a excitation purity.

Respective three stimulus values in the high light part and shade part are obtained. From the three stimulus values $X_1$, $Y_1$, and $Z_1$ in the high light part, $x_1$ $[=X_1/(X_1+Y_1+Z_1)]$ and $y_1$ $[=Y_1/(X_1+Y_1+Z_1)]$ are calculated and, from the three stimulus values $X_2$, $Y_2$, $Z_2$ in the shade part, $x_2$ $[=X_2/(X_2+Y_2+Z_2)]$ and $y_2$ $[=Y_2/(X_2+Y_2+Z_2)]$ are calculated, whereby their respective chromaticity coordinates are obtained and, as seen in FIG. 7, are plotted in the chromaticity diagram. The lines $l_1$ and $l_2$ connecting with the light source point n are drawn, the $l_{1a}$, $l_{1b}$, $l_{2a}$, and $l_{2b}$ are measured with a ruler, and calculations of the $l_{1a}/l_{1b}$ and $l_{2a}/l_{2b}$ values results in their respective excitation purities.

The method in the present invention is not limited within the forementioned. For example, an object for evaluating the color tone may be a coating film which consists of only the down layer 1'.

The device in the present invention which is used for getting data is not limited with only the construction as shown in FIG. 2.

Figure 3:
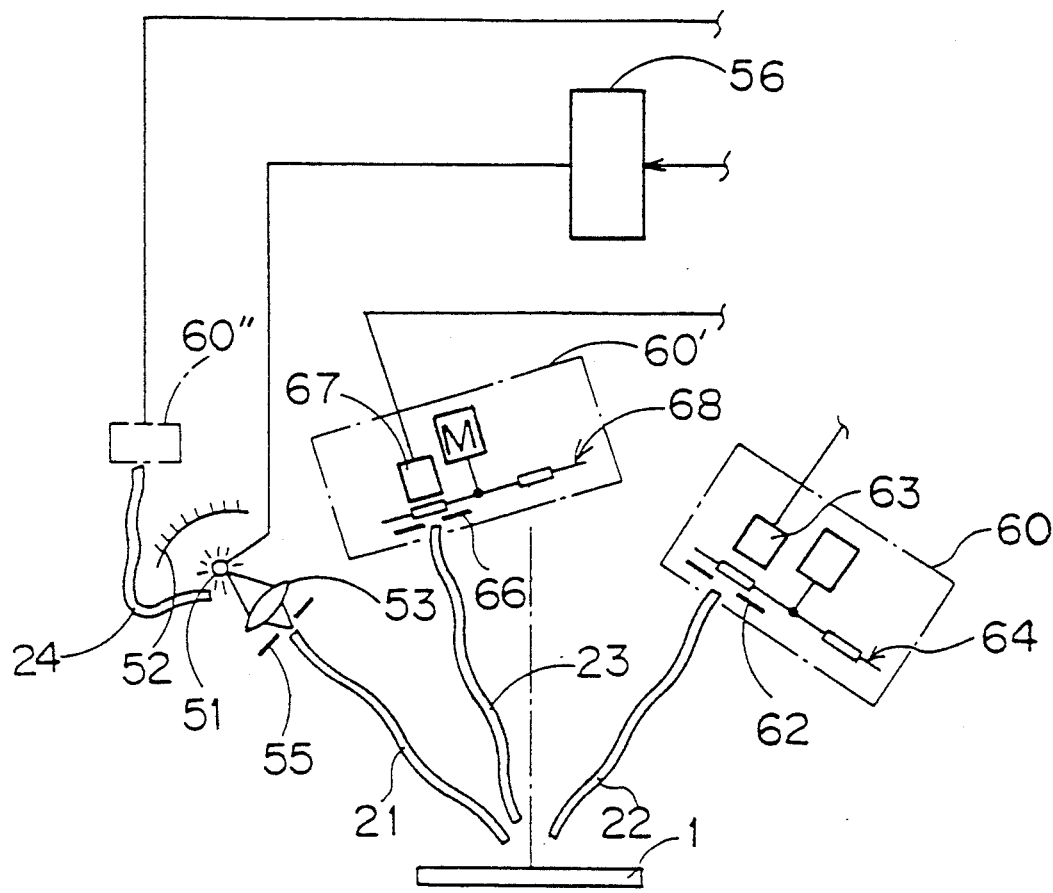
FIGS. 3, 4, and 9 are typical diagrams which show other composition examples around a photoelectric detector in a device of this invention.

For example, as seen in FIG. 3, a light of the light source 51 may be conducted onto a coating film by the optical fiber 21, the high light part and shade part may also be conducted to the spectral means 64 and 68 by the optical fibers 22 and 23, and a light of the light source 51 may be conducted to the spectrospic detecting part 60" by the optical fiber 24.

Figure 4:
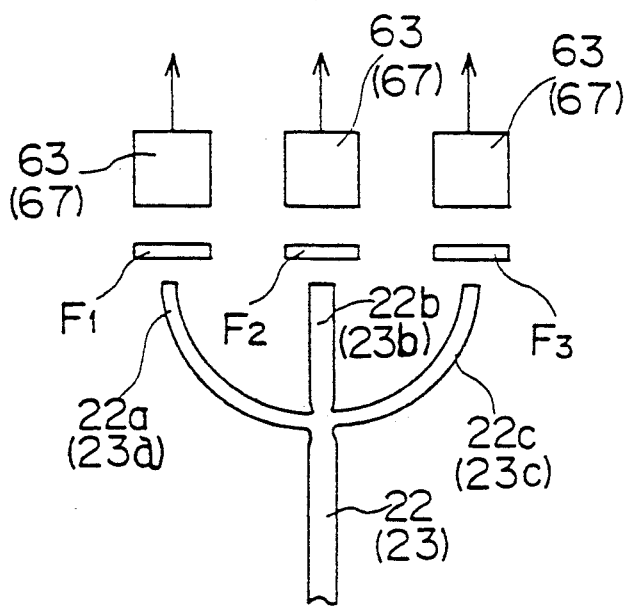

Furthermore, as seen in FIG. 4, the number of light detector elements in each spectrospic detecting part is set as 3 and the filters $F_1$, $F_2$, and $F_3$ which are, respectively, set up in front of each element are arranged as the spectral means. Thus, for example, by dividing an end of the optical fiber 22 (23) into three branches 22a (23a), 22b (23b), and 22c (23c), or by using a half mirror, the reflecting light is divided into three which are respectively and simultaneously projected into the light detector elements. In this case, filter-switching may be omitted.

Figure 9:
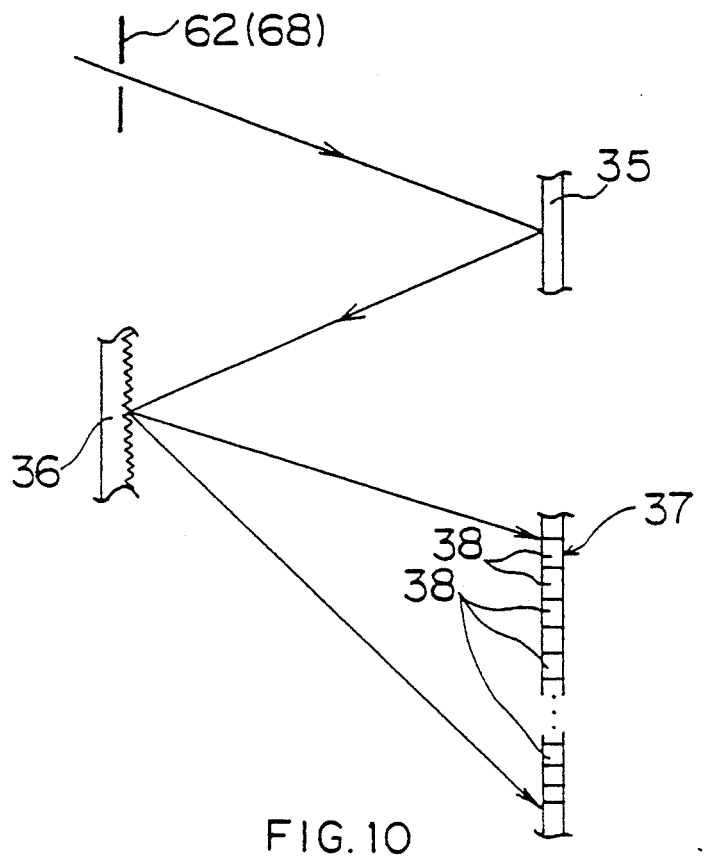

Outputs of the light detecting elements need not to be detecting signals which correspond to the three stimulus values X, Y, and Z. For example, as seen in FIG. 9, the light being projected into the element is conducted by a mirror 35 to a diffraction grating 36, with which (or a prism) it is separated and conducted to a photodiode array 37, whereby spectral photoelectrically detected signals are obtained and sent to a microprocessor, and the three stimulus values may be derived with calculation with the microprocessor. Needless to say, the photodiode array 37 is equipped with a number of diodes 38 ... which are set up in series at a pitch of a constant wave length (for example, 20 nm) and, from each diode, the photoelectrically detected signals due to lights having the corresponding wave lengths are outputted.

Figure 8:
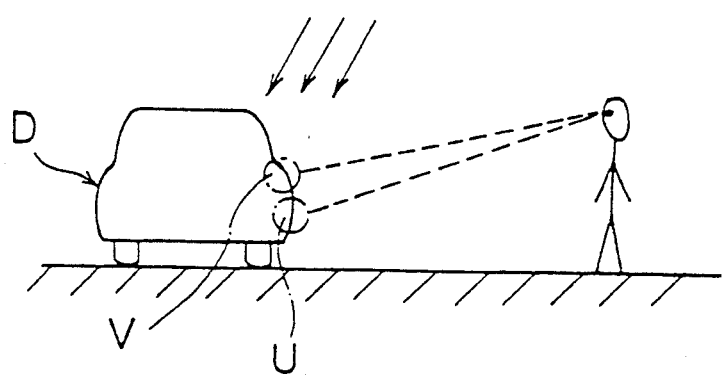
FIG. 8 is a typical diagram which explains a coexisting situation of both the cases that are seen from the high light direction and from the shade direction.

In a method of the present invention, the saturation and/or excitation purity of a high light part, and, if necessary, those of a shade part are checked. Evaluation based on data of the saturation or excitation purity reflects well a deepness feeling and a transparency feeling. Also, in the device in the present invention, this evaluation can be carried out in both cases of that a coating film is seen from a shade direction and from a high light direction. In a case of a coating film of an automobile body, as seen in FIG. 8, since the region U seen in the shade direction and the region V seen in the high light direction coexist, the evaluation is necessary for the cases of both regions of U and V, but evaluation results of both the cases are obtained in the device of the present invention and, therefore, sufficient response is obtainable in the cases of this kind. Besides, in a case of that evaluation based on the differences in lightness, color, and luminous intensity is also carried out, the evaluation results may reflect the contrast feeling as well.

Referring to a practical coating, as seen in FIG. 5 (a), the surfaces of the down layer 1' and upper layer 1'' of the coating film 1 are smooth and a gloss material is oriented in a parallel direction to the surfaces, a light projected into the coating film results in little reflection on the coating film surface and largely enters into the coating film, and thus, in a case of that light-scattering and light-absorption on the clear layer (the upper layer) 1'' and light-scattering on an interface between the upper layer 1'' and the down layer 1' are small, the contrast, deepness, and transparency feelings are enhanced. However, as seen in FIG. 5 (b), the saturation and excitation purity are low and the contrast, deepness, and transparency feelings are lacking in a case of that the surfaces of the down layer 1' and upper layer 1'' are waved and bad in smoothness, the orientation of a gloss material is bad, and a light projected into a coating film shows large reflecting proportion on a coating film surface and small proportion of a light entering into a coating film, and light-scattering and light-absorption on the clear layer (the upper layer) 1'' and light-scattering on an interface between the upper layer 1'' and the down layer 1' are large.

Next, practical examples are explained.

The undermentioned coating films ① to ⑦ were taken as objects for evaluating color tones. The data for evaluating color tones were taken by the forementioned device in FIG. 2.

The data obtained from the coating films ① to ⑦ are as presented in Table 1.

The data obtained are the high light saturation $C^*ab(H)$, high light excitation purity PH, shade saturation $C^*ab(S)$, shade excitation purity PS, $\Delta L^*$, and $\Delta E^*ab$. The high light excitation purity PH and $\Delta E^*ab$ were plotted on a graph in FIG. 10, taking $\Delta E^*ab$ as the axis of abscissas and the high light excitation purity as the axis of ordinates. Also, the high light saturation $C^*ab(H)$ and $\Delta E^*ab$ were plotted on a graph in FIG. 11, taking $\Delta E^*ab$ as the axis of abscissas and the high light saturation as the axis of ordinates.

However, the measurement of the high light part is carried out with an incident angle of $-45°$ and a light-receiving angle of 35° (10° against a regularly reflecting light), and the measurement of the shade part is carried with an incident angle of $-45°$ and a light-receiving angle of 0° (45° against a regularly reflecting light).

Coating film ①

(a) Down layer paint: an acryl resin paint of a melamine-crosslinking type in which a red pigment of high transparency and a colored mica flake pigment are arranged.
(b) Thickness of the down layer film: 15 μm
(c) Upper layer paint: a transparent acryl resin paint of a melamine-crosslinking type
(d) Thickness of the upper layer film: 35 μm
(e) Time interval before coating of the upper layer paint: 4 minutes Coating Film ②

(a) Down layer paint: same to that of the coating film ①
(b) Thickness of the down layer film: 15 μm
(c) Upper layer paint: same to that of the coating film ①
(d) Thickness of the upper layer film: 35 μm
(e) Time interval before coating of the upper layer paint: 24 hours Coating Film ③

(a) Down layer paint: same to that of the coating film ①
(b) Thickness of the down layer film: 15 μm
(c) Upper layer paint: same to that of the coating film ①
(d) Thickness of the upper layer film: 35 μm
(e) Time interval before coating of the upper layer paint: none Coating Film ④

(a) Down layer paint: same to that of the coating film ①, but a dispersing degree of the pigment is high.
(b) Thickness of the down layer film: 15 μm
(c) Upper layer paint: same to that of the coating film ①
(d) Thickness of the upper layer film: 35 μm
(e) Time interval before coating of the upper layer paint: same to the case of coating film ①

Coating Film ⑤

(a) Down layer paint: a paint in which the pigment in the paint of coating film ① is changed into the one having higher saturation and higher transparency.
(b) Thickness of the down layer paint: 15 μm
(c) Upper layer paint: same to that of the coating film ①
(d) Thickness of the upper layer film: 35 μm
(e) Time interval before coating of the upper layer paint: same to the case of coating film ①

Coating Film ⑥

(a) Down layer paint: a paint in which the colored mica flake pigment in the paint of coating film ⑤ is changed into the one having higher gloss performance.
(b) Thickness of the down layer film: 15 μm
(c) Upper layer paint: same to that of the coating film ①
(d) Thickness of the upper layer film: 35 μm
(e) Time interval before coating of the upper layer paint: same to the case of coating film ①

Coating Film ⑦

(a) Down layer paint: same to that of the coating film ⑥
(b) Thickness of the down layer film: 15 μm
(c) Upper layer paint: a paint wherein a red pigment of high transparency is contained in a low concentration into the paint of coating film ①.
(d) Thickness of the upper layer film: 35 μm
(e) Time interval before coating of the upper layer paint: same to the case of coating film ①.

Furthermore, the coating conditions of the upper and down layers are as follows.

Down Layer

A paint which is adjusted at a stipulated viscosity (#4 Ford cup 22 seconds/20° C.) is coated, according to an air spraying method (a wider #71 model, made by Iwata Tosoki Co., Ltd., an initial pressure 4 kg/cm$^2$), so as to form a stipulated film thickness.

Upper Layer

A paint which is adjusted at a stipulated viscosity (#4 Ford cup 13 seconds/20° C.) is coated, according to a air spraying method (a wider #71 model, made by Iwata Tosoki Co., Ltd., an initial pressure 4 kg/cm$^2$), so as to form a stipulated film thickness.

TABLE 1

|  | C*ab (H) | PH (%) | C*ab (S) | PS (%) | ΔL* | ΔE*ab |
|---|---|---|---|---|---|---|
| Coating film ① | 39.26 | 37.5 | 43 | 73.2 | 15.41 | 15.50 |
| Coating film ② | 55.23 | 72.4 | 49 | 76.1 | 17.67 | 22.82 |
| Coating film ③ | 38.75 | 56.2 | 41 | 74.4 | 5.8 | 7.10 |
| Coating film ④ | 49.67 | 58.3 | 48 | 76.2 | 13.94 | 17.02 |
| Coating film ⑤ | 58.35 | 51.2 | 48 | 72.8 | 25.43 | 31.23 |
| Coating film ⑥ | 76.83 | 61.1 | 51 | 75.7 | 36.45 | 50.99 |
| Coating film ⑦ | 80.19 | 66.4 | 53 | 78.0 | 32.89 | 51.05 |

Figure 10:
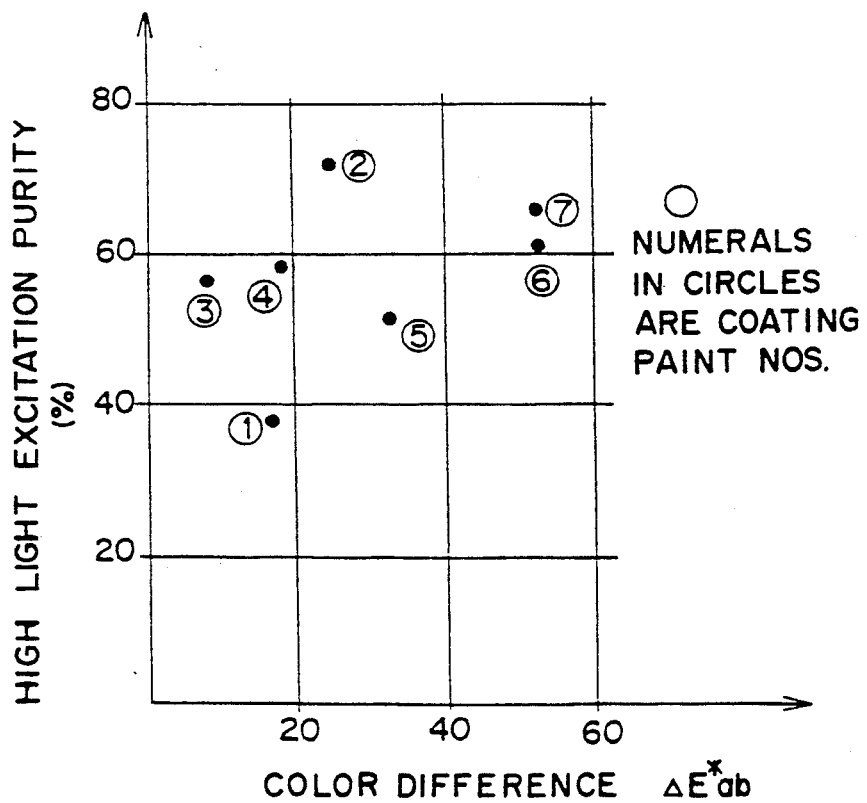
FIG. 10 is a graph which shows a relation of the high light excitation purity PH with the color difference $\Delta E^*ab$ in the coating films ① to ⑦.
Figure 11:
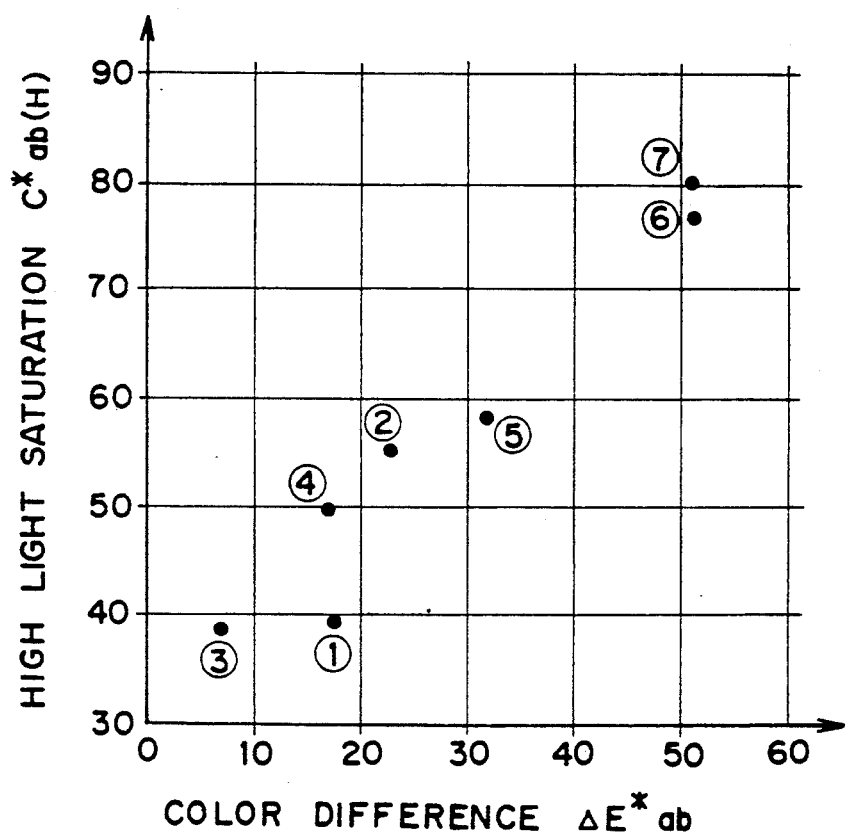
FIG. 11 is a graph which shows a relation of the high light saturation $C^*ab(H)$ in the coating films ① to ⑦ with the color difference $\Delta E^*ab$.

FIGS. 10 and 11 were prepared to see an interrelation of the excitation purities and saturation at high light parts of said coating films ① to ⑦ with the color difference. It is clear from the graphs that there is no satisfactory interrelation between the ΔE*ab which represents the contrast feeling and the excitation purity and saturation which represent the deepness and transparency feelings.

As seen in these figures, the coating films ⑥ and ⑦ show almost no color difference, but when looking at the saturation and excitation purity, the coating film ⑦ is superior to the coating film ⑥. In other words, the coating film ⑦ is in the same grade as the coating film ⑥ in a point of the contrast feeling, but the film ⑦ is superior to the film ⑥ in points of the deepness and transparency feelings. the observation results by ten panelists led to an indication that the coating film ⑦ has a better appearance than the coating film ⑥. In the method for evaluating in the present invention, even in the coating films which show no difference in the contrast feeling as mentioned above, it is possible to get an evaluation result which suggests some meaningful difference (superior or inferior) in the deepness and transparency feelings and, as a result, sufficiently high evaluation can be obtained. That the deepness and tenasparency feelings can not be evaluated with sufficient correctness by only looking at the contrast feeling is easily seen in the graphs of FIGS. 10 and 11. Besides, it was confirmed that the results obtained from evaluation of the deepness and transparency feelings with eyes have shown a good relationship with high or low values obtained from measurements of the saturation and color stimulus value.

As so far mentioned, since in the present invention the saturation and excitation purity are measured in the high light direction and, if necessary, the shade direction, not only superiority or inferiority of the deepness and transparency feelings is reflected well on the evaluation results of the color tone, but also evaluations are possible in both cases of that a coating film is seen in a high light direction and that a coating film is seen in a shade direction and, therefore, very useful evaluation results can be obtained.

What is claimed is:

1. A method for evaluation of a color tone of a coating film, comprising the steps of projecting a luminous flux on a coating film, obtaining light reflected from said coating film; the reflected light including a regularly reflected luminous flux, obtaining a high light excitation purity of the coating film on a basis of a high light part of the reflected light which is at an angle of about 10° against the regularly reflected luminous flux in the reflected light, and deriving a transparency feeling and a deepness feeling of the coating film from said high light excitation purity.

2. The method of claim 1, in which at least one of color difference, lightness difference, and luminous intensity difference between said high light part and a shade part of the reflected light which is at an angle in a range exceeding 15° against the regularly reflected luminous flux in the reflected light, is used in the evaluation of the color tone of the coating film.

* * * * *